United States Patent [19]

Marwil

[11] 4,302,604

[45] Nov. 24, 1981

[54] INCREASING THE LIFE OF A SUPPORTED RUTHENIUM CATALYST IN THE HYDROGENATION OF AN OLEFINICALLY UNSATURATED DINITRILE

[75] Inventor: Stanley J. Marwil, Bartlesville, Okla.

[73] Assignee: Phillips Petroleum Company, Bartlesville, Okla.

[21] Appl. No.: 171,921

[22] Filed: Jul. 24, 1980

[51] Int. Cl.³ .............................................. C07C 85/12
[52] U.S. Cl. ..................................... 564/491; 564/511
[58] Field of Search ........................................ 564/491

[56] References Cited

U.S. PATENT DOCUMENTS

| | | | |
|---|---|---|---|
| 3,369,997 | 2/1968 | Hayes et al. | 208/139 |
| 3,408,397 | 10/1968 | Feldman et al. | 564/491 |
| 3,896,173 | 7/1975 | Drake | 564/491 |
| 3,953,511 | 4/1976 | Frech et al. | 564/491 |

*Primary Examiner*—Robert V. Hines

[57] ABSTRACT

In a process for hydrogenating an olefinically unsaturated dinitrile in which the reactants in a solvent are passed through a ruthenium on alumina catalyst, the improvement which comprises operating at a reduced pressure during the early contact with the catalyst and slowly increasing the pressure over an extended interval of time to normal operating pressure. This startup procedure greatly increases the run length (life) of the catalyst bed.

11 Claims, No Drawings

INCREASING THE LIFE OF A SUPPORTED RUTHENIUM CATALYST IN THE HYDROGENATION OF AN OLEFINICALLY UNSATURATED DINITRILE

FIELD OF THE INVENTION

The invention pertains to a method to increase the effective life of a supported ruthenium catalyst. In another aspect, the invention pertains to a method to increase the run length of a hydrogenation process for conversion of unsaturated dinitriles to saturated diamines employing a supported ruthenium catalyst.

BACKGROUND OF THE INVENTION

Supported ruthenium catalysts utilizing a solvent system have provided generally effective hydrogenation of olefinically unsaturated dinitriles.

Unfortunately, these supported ruthenium catalysts in practice have had a relatively short run life, and have proven very difficult to regenerate. In fact, upon fouling or deactivation, the supported catalyst usually has been simply dumped from the contactor and returned to the manufacturer for reclaiming of the valuable ruthenium. Not only is this a material-costly procedure, but short run life means more frequent down times, and the handling of the catalyst means a labor cost intensive operation despite the theoretically efficiency of the hydrogenation process when it is running satisfactorily.

Badly needed has been method to extend the run life, useful catalyst life, of the supported ruthenium catalyst in the hydrogenation of olefinically unsaturated dinitriles.

BRIEF DESCRIPTION OF THE INVENTION

In accordance with my process, the run life, the useful catalyst life, of a supported ruthenium catalyst has been dramatically increased in its application for the hydrogenation of olefinically unsaturated dinitriles to the corresponding diamines.

My process employs a low pressure startup process, operating the hydrogenation system at a reduced pressure during the early life of the run, slowly increasing the pressure over an extended interval of time, finally up to the normal operating pressure. This procedure greatly increases the run length of the catalyst bed, and stretches considerably the operating time between outages for replacement of catalysts.

DETAILED DESCRIPTION OF THE INVENTION

Early fouling and/or deactivation of supported ruthenium hydrogenation catalysts has been the usual situation, though these catalysts, particularly the ruthenium-on-alumina catalysts, have proven quite effective in the hydrogenation of olefinically unsaturated dinitriles to the corresponding diamines. Reactivation procedures generally have been ineffective. The cause of the deactivation has not been pinned down, though it has been suggested that during otherwise attempted regenerations, such as varying procedures of temperature/gaseous exposure and the like, the ruthenium metals may tend to migrate to form relatively large crystallites with a reduced metal surface area and hence reduced activity, an apparently not readily reversible process.

In accordance with my procedure, I obtain significantly increased run life, longer useful ruthenium catalyst life in a hydrogenation process, by commencing the process of hydrogenation of the olefinically unsaturated dinitrile at a reduced pressure during the early stage of operation of the system, slowly increasing the pressure over an extended interval of time, preferably over several hours, gradually approaching normal operating pressure. This procedure at least doubles the run length of the ruthenium catalyst for hydrogenation purposes.

Catalysts

The catalyst is a supported ruthenium catalyst comprising ruthenium on a solid support. Supports which can be used include carbon, kieselguhr, silica, alumina, silica-alumina, calcium carbonate, barium carbonate, asbestos, pumice, clays, and the like, including mixtures. Presently preferred is alumina, preferably α-alumina. While it is presumed that the ruthenium is present as the metal element, I do not wish necessarily to be bound by such presumption, since the catalyst can be prepared from catalytic amounts of the elemental metal, or reducible compounds of the metal, or mixtures, in preparing the supported catalyst.

The elemental metal or reducible compounds of ruthenium can be added to the catalyst support by any methods known in the art. For example, the supported catalyst can be prepared by dry mixing a suitable component or components, or by impregnating the support with a solution or dispersion of the metal catalyst in elemental form or in the form of reducible compounds thereof. The supported catalyst can be pretreated with hydrogen to reduce the compounds or such reduction even can be achieved ultimately by hydrogenation in situ in the hydrogenation process reactor.

The total catalyst, i.e., the ruthenium-on-support, generally will contain in the range of about 0.1 to 50 weight percent ruthenium expressed as the metal relative to the total of ruthenium and support, preferably in the range of about 0.1 to 10 weight percent. Presently preferred is ruthenium representing about 0.5 percent by weight relative to the total of ruthenium plus support.

Reactor Feed

Preferred feed for the hydrogenation reaction is made up of one or more branched chain unsaturated aliphatic dinitriles of the formula:

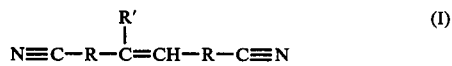

wherein each R is independently selected from the group consisting of an alkylene radical and an alkylidene radical and R' is an alkyl radical. Each R will generally have from one to fifteen carbon atoms, preferably from one to six, and more preferably from one to three carbon atoms. R' generally will have from one to fifteen carbon atoms, preferably from one to six, and more preferably from one to three carbon atoms. In general, the unsaturated dinitrile reactant of formula (I) will contain from seven to 30 carbon atoms, preferably from eight to 16 carbon atoms, and preferably from nine to 12 carbon atoms.

Representative of unsaturated reactant species of formula (I) include such compounds as 4-methyl-3-hexenedinitrile, 4-ethyl-3-hexenedinitrile, 5-methyl-4-nonenedinitrile, 5-ethyl-4-decenedinitrile, 7-methyl-6- tridecenedintrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-5,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures thereof.

If desired, other unsaturated dinitrile reactants can be present and effectively hydrogenated during the hydrogenation of the unsaturated dinitriles of formula (I). Thus, in addition to the unsaturated dinitrile reactants of formula (I), the dinitrile feedstock can contain one or more unsaturated dinitrile reactants of the formula:

(II)

wherein each R" is independently selected from the group consisting of an alkylene radical and an alkylidene radical. In general, each R" will have from one to 15 carbon atoms, preferably from one to seven carbon atoms, and more preferably from one to four carbon atoms. The dinitriles of formula (II) will generally contain from six to 30 carbon atoms, preferably from eight to 16 carbon atoms, and more preferably from nine to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures thereof.

Unsaturated dinitriles having a structure other than that of formulae (I) and (II) can be present during the hydrogenation reaction, if desired. Similarly, other compounds which may be found in the feed source of the dinitriles of formulae (I) and (II) can be present so long as such additional compounds do not significantly adversely affect the hydrogenation of the dinitriles of formulae (I) and (II). Where other dinitriles are present in the feedstock, the dinitriles of formula (I) generally constitute at least about 0.1 weight percent of the total dinitriles. A presently most preferred branched-chain unsaturated aliphatic dinitrile feedstock is the dinitrile reaction product mixture obtained by the reaction of isobutylene and acrylonitrile. This dinitrile reaction product mixture comprises 5-methyl-4-nonenedinitrile, 2,4-dimethyl-4-octenedinitrile, 2,4-dimethyl-3-octenedinitrile, 2,4,6- trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture generally is in the range of about 10:1 to 1:10.

The catalytic hydrogenation of the unsaturated dinitrile reactant of formula (I) results primarily in the formation of saturated diamine reaction products having the formula:

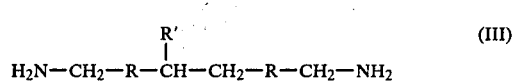
(III)

wherein R and R' are as previously defined. The catalytic hydrogenation of an unsaturated dinitrile reactant of formula (II) results primarily in the formulation of saturated diamine reaction products having the formula:

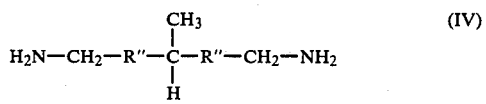
(IV)

wherein R" is as previously defined.

Hydrogenation Reaction Conditions

The hydrogenation process can be conducted in a single reactor means, though more usually two reactor means operated in series are employed, sometimes with a third operating as standby. A series operation of two reactor means tends to provide substantially complete saturation of the olefinically unsaturated dinitrile, of both the nitrile groups as well as the olefinically double bond, with improved results over a single reactor means. In a multiple means type operation, one reactor means can be taken off the line for removal of the supported catalyst as hereinbefore described, while the other reactor means continues the operation, and, preferably, the third or alternate reactor means can be put into line to maintain a series system. Dehydrogenation preferably is conducted as a continuous process.

The weight ratio of catalyst to unsaturated dinitrile can be any suitable change and is affected by liquid hourly space velocity, particular temperatures employed, and the like. In general, in each reactor means the weight ratio of catalyst, calculated as elemental ruthenium metal to feed compounds to be hydrogenated, usually is in the range of about 0.001:100 to 30:100, more usually in the range of about 0.01:100 to 5:100.

The liquid hourly space velocity employed generally will be in the range of about 0.1 to 20, more usually about 0.5 to 10, LHSV volumes of unsaturated dinitrile reactant plus diluent and ammonia per volume of catalyst (including volume of catalyst support).

Diluents employed in the hydrogenation of branched chain unsaturated aliphatic dinitriles are usually selected from aliphatic tertiary alcohols, acyclic and cyclic ethers, and saturated hydrocarbons. Examples include 2-methyl-2-propanol (t-butyl alcohol), 2-methyl-2-butanol, dipropyl ether, 1,4-dioxane, dodecane, cyclododecane, cyclohexane, and the like, and mixtures thereof. The weight ratio of unsaturated dinitrile reactants to diluent charged to the reaction zone is generally within the weight ratio of about 1:9 to 1:11, and is preferably about 1:10.

Ammonia normally is employed as a means of suppressing undesirable side reactions such as the formation of secondary and tertiary amines. Any amount of ammonia as secondary amine formation suppressant can be employed which is effective in deterring or reducing undesirable side reactions. In general, the weight ratio of secondary amine formation suppressant to unsaturated dinitrile reactants will be in the range of about 0.5:1 to 2:1, preferably about 1:1.

Any catalytically effective hydrogenation temperature can be employed which provides the desired degree of efficiency in the hydrogenation of the unsaturated dinitrile feedstock. Generally the hydrogenation temperature during the low pressure phase in my inventive process will be lower than employed during the normal operating phases. Thus, hydrogenation temperatures can be employed in the broad range of about 100° C. to 175° C., while the hydrogenation temperature during the low pressure phase of my invention is in the range of between about 100° C. and 120° C., and during normal operation is generally in the range of about 100° C. to 170° C., but more usually 120° C. to 150° C.

Reaction times should be sufficient to achieve the substantially complete degree of hydrogenation desired, and will be affected by temperature, liquid, hourly space velocity, as well as pressure, as can be recognized by the art.

In accordance with my invention, system operating pressure at the beginning of the hydrogenation reaction will be in the range of about 900 to 1300 psia, more preferably about 1200 to 1300 psia, achieved by the combination of olefinic dinitrile and hydrogen. Employed is a relationship of about 0.5 to 1.5, more preferably about 0.9 to 1.1, SCFM of hydrogen:lb/hr of olefinic dinitrile.

In accordance with my invention, after operating the hydrogenation process at the reduced pressure from about 1 to 160 hours, the pressure is slowly increased over a 24 to 48 hour interval until the normal operating pressure is reached. Normal operating pressure is in the range of about 1500 to 2500 psia, more usually about 1500 to 1600 psia.

Recovery of the desired end product from the hydrogenation of branched chain unsaturated dinitriles, the branched chain saturated diamines, as well as any resulting reaction byproducts, any unconsumed reactants, ammonia, hydrogen, and/or diluents, can be carried out by any conventional separation means. The recovered diluent and ammonia can be recycled to the hydrogenation zone, if desired. The saturated diamines can be separated from any reaction byproducts or any remaining diluent by any conventional fractional distillation.

EXAMPLES

Examples following are intended to further illustrate the scope of my invention. Particular components employed, amounts, species, relationships, conditions, and the like, should be considered, as illustrative and not limitative of the reasonable scope of my invention as herein disclosed and claimed.

EXAMPLE I

In each of a series of runs, two 3-inch by 10-foot (approximately 0.5 cu. ft. each) pilot plant reactors in series were packed with a mixture of a commercially available 0.5 wt.% ruthenium catalyst on an α-alumina catalyst support. The reactant feed was a mixture of isomeric unsaturated dinitriles having one carbon-carbon double bond and 10 carbon atoms per molecule. The principal isomers were 5-methylenenonanedinitrile and 5-methyl-4-nonenedinitrile with small amounts of more highly branched isomers such as 2-methyl-4-methyleneoctanedinitrile, among others. For simplicity the above-described reactant feed will hereafter be called diadduct. The diadduct feed rate was 4.0 lb./hr.

Two solvent mixtures were used during the tests, an 88 wt. % t-butyl alcohol-12 wt. % water and a 37 wt. % t-butyl alcohol-63 wt. % cyclohexane mixture. The solvent rate to the reactor was 36.0 lb./hr.

Ammonia was fed to the reactor at a rate of 4.0 lb./hr. and hydrogen at 3.7 SCFM. The reaction temperature ranged from 120° C. to 160° C. additional operating conditions and results are set forth in Table I:

TABLE I

| Run | Lbs. of Catalyst[a] | Dilution of Catalyst | Solvent | Reactor Low Pressure PSIG | Hrs. at Low Pressure | Reactor High Pressure PSIG | Length of Run, Hrs. |
|---|---|---|---|---|---|---|---|
| 1 | 42 | 2/1[b] | (d) | — | 0 | 1600 | 89 |
| 2 | 24 | 2/1[c] | (d) | 1300 | 48 | 1600 | 242 |
| 3 | 24 | 4/1[c] | (d) | 1300 | 72 | 1600 | 254 |
| 4 | 34.5 | 1/1[b] | (e) | — | 0 | 1500 | 181 |
| 5 | 42 | 2/1[b] | (e) | 1300 | 48 | 1600 | 197 |
| 6 | 43 | 2/1[b] | (e) | 1300 | 60 | 1600 | 301.5 |
| 7 | 42 | 2/1[b] | (e) | 1350 | 140 | 1600 | 455.0 |

[a].05 wt. % ruthenium on alumina catalyst (C-7093, Engelhard Minerals & Chemicals Corp. New York, New York).
[b]Catalyst diluted with inert α-alumina catalyst support (SA-5123, Norton Chemical Process Products, Akron, Ohio).
[c]Catalyst diluted with inert α-alumina catalyst support (L-101, United Catalysts Inc., Louisville, Kentucky).
(d)88 wt. % t-butyl alcohol - 12 wt. % water.
(e)37 wt. % t-butyl alcohol - 63 wt. % cyclohexane.

The disclosure, including data, illustrate the value and effectiveness of my invention. The Examples, the knowledge and background of the field of the invention, as well as the general principles of chemistry and other applicable sciences, have formed the bases to which the broad description of the invention including the range of conditions and generic groups of operate components have been developed, and further formed bases for my claims here appended.

I claim:

1. In a single-stage process for the reduction of olefinically unsaturated dinitriles to saturated diamines by contacting a supported ruthenium catalyst, olefinically unsaturated dinitrile, hydrogen, diluent, and ammonia as secondary amine suppressant, under effective hydrogenation conversion run conditions of contacting temperature in the range of about 100° C. to 170° C., and contacting pressure in the range of about 1500 to 2500 psia, the improvement which comprises increasing the run life of said supported ruthenium catalyst by initially contacting said supported ruthenium catalyst, olefinically unsaturated dinitrile, hydrogen, diluent, and ammonia at a low contacting pressures in the range of about 900 to 1300 psig for a start-up interval of 1 to about 160 hours at a start-up temperature in the range of about 100° C. to 120° C., and thereafter gradually increasing the operating pressure over an interval of about 24 to 48 hours to said run operating pressure, thereby increasing the run life of said supported ruthenium catalyst for said single-step reduction process.

2. The process according to claim 1 wherein said initial low contacting operating pressure is in the range of about 1200 to 1300 psia, and said run operating pressure is in the range of about 1500 to 1600 psia.

3. The process according to claim 2 employing a hydrogenation temperature during normal run operation in the range of about 120° C. to 150° C., a liquid hourly space velocity in the range of about 0.1 to 20 volumes of unsaturated dinitrile plus diluent plus ammonia per volume of ruthenium catalyst including support.

4. The process according to claim 3 wherein the support for said supported ruthenium catalyst is selected from the group consisting of carbon, kieselguhr, silica, alumina, silica-alumina, calcium carbonate, barium carbonate, asbestos, pumice, and clay; and
wherein said supported ruthenium catalyst contains 0.1 to 50 weight percent ruthenium relative to the total of ruthenium plus support.

5. The process according to claim 4 wherein said diluent is selected from the group consisting of aliphatic tertiary alcohols, acyclic and cyclic ethers, and saturated hydrocarbons.

6. The process according to claim 5 wherein said olefinically unsaturated dinitrile comprises at least one branched chain unsaturated aliphatic dinitrile represented by the formula:

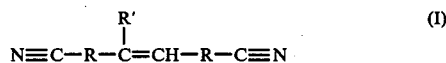

optionally with

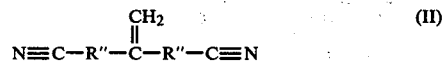

wherein each R is independently selected from the group consisting of an alkylene radical and an alkylidene radical, R' is an alkyl radical, R" is independently selected from the group consisting of an alkylene radical and an alkylidene radical, such that each R has one to 15 carbon atoms, R' 1 to 15 carbon atoms, R" 1 to 15 carbon atoms.

7. The process according to claim 6 wherein each R has 1 to 6 carbon atoms, each R' 1 to 6 carbon atoms, and each R" 1 to 7 carbon atoms.

8. The process according to claim 6 wherein said unsaturated dinitrile is selected from the group consisting of 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-5,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures, and optionally can contain one or more of 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures thereof.

9. The process according to claim 8 wherein said olefinically unsaturated dinitrile comprises a mixture of isomeric unsaturated dinitriles having one carbon-carbon double bond and 10 carbon atoms per molecule, and said supported ruthenium catalyst is ruthenium-on-alumina containing 0.1 to 10 weight percent alumina.

10. The process according to claim 9 wherein the principal isomers comprise 5-methylenenonenedinitrile and 5-methyl-4-nonenedinitrile.

11. The process according to claim 10 wherein said supported ruthenium catalyst is ruthenium-on-α-alumina containing about 0.5 weight percent ruthenium.

* * * * *